(12) United States Patent
Kakol et al.

(10) Patent No.: US 8,404,828 B2
(45) Date of Patent: Mar. 26, 2013

(54) NON-NATURALLY OCCURRING DNA SEQUENCES

(75) Inventors: Jerzy Kakol, San Diego, CA (US); Tobias Mann, Carlsbad, CA (US); Timothy K. McDaniel, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 420 days.

(21) Appl. No.: 12/757,805

(22) Filed: Apr. 9, 2010

(65) Prior Publication Data

US 2011/0250697 A1    Oct. 13, 2011

(51) Int. Cl.
*C07H 21/02* (2006.01)
*C07H 21/04* (2006.01)
*C12Q 1/68* (2006.01)

(52) U.S. Cl. .................................. 536/24.3; 435/91.1
(58) Field of Classification Search .................. None
See application file for complete search history.

(56) References Cited

PUBLICATIONS

GenomeQuest comprehensive search report on SEQ ID No. 1-40, performed Mar. 24, 2010.

*Primary Examiner* — Jehanne Sitton
(74) *Attorney, Agent, or Firm* — Brent C. Moore

(57) ABSTRACT

DNA compositions having nucleotide sequences that do not occur in nature. Also provided are fluorescently labeled DNA molecules and complementary DNA on solid substrates, such as microspheres.

20 Claims, No Drawings

SEQUENCE LISTING

```
<160> NUMBER OF SEQ ID NOS: 40

<210> SEQ ID NO 1
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 1
aatacgcatc gacggttgtc cccga                                        25

<210> SEQ ID NO 2
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 2
aatttactgg ccttacggta gtaca                                        25

<210> SEQ ID NO 3
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 3
acgcatatgt cagaggaaat tgcac                                        25

<210> SEQ ID NO 4
<211> LENGTH: 25
```

```
<212> TYPE: DNA
<213> ORGANISM: Artificial Sequence
<220> FEATURE:
<223> OTHER INFORMATION: non-naturally occurring sequence

<400> SEQUENCE: 4
actcgtggtt taatccagca tcgtc                                              25

<210> SEQ ID NO 5
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 5
agttttagat tgagttctac gtcga                                              25

<210> SEQ ID NO 6
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 6
ataaccctca aacgtagggc agatg                                              25

<210> SEQ ID NO 7
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 7
ataattgacg gcgcgtagcc cgtcg                                              25

<210> SEQ ID NO 8
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 8
attggaggct acgttggtct aacat                                              25

<210> SEQ ID NO 9
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 9
atttctagtc ggcgtagacg catgt                                              25

<210> SEQ ID NO 10
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 10
caagacgtca acgcgagaca cggca                                              25
```

```
<210> SEQ ID NO 11
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 11
cacggaacct cggcgttggc gtcta                                      25

<210> SEQ ID NO 12
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 12
cagttgacgt gcagtcaccc acgca                                      25

<210> SEQ ID NO 13
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 13
catttaccga acaaaattga tacgt                                      25

<210> SEQ ID NO 14
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 14
ccaatttccg cgcagtgatt agatg                                      25

<210> SEQ ID NO 15
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 15
ccgcacttaa agaattgatg accgt                                      25

<210> SEQ ID NO 16
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 16
cgagaacgtt tggttgagaa tccat                                      25

<210> SEQ ID NO 17
<211> LENGTH: 25
<212> TYPE: DNA
<213> ORGANISM: Artificial Sequence
<220> FEATURE:
<223> OTHER INFORMATION: non-naturally occurring sequence
```

```
<400> SEQUENCE: 17
cggtgagctg cgaaggcggt acgcg                                          25

<210> SEQ ID NO 18
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 18
ctctaaacgc tagcttaggt cttct                                          25

<210> SEQ ID NO 19
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 19
cttggtctcg aattgtgccc tagaa                                          25

<210> SEQ ID NO 20
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 20
gaccggtgga acactgccac aacat                                          25

<210> SEQ ID NO 21
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 21
gagttaacaa tttaccacgt ttaga                                          25

<210> SEQ ID NO 22
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 22
gatacgggac ttctaacagt gactc                                          25

<210> SEQ ID NO 23
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 23
gcctagagag ccactcagag cacta                                          25

<210> SEQ ID NO 24
<211> LENGTH: 25
```

```
<212> TYPE: DNA
<213> ORGANISM: Artificial Sequence
<220> FEATURE:
<223> OTHER INFORMATION: non-naturally occurring sequence

<400> SEQUENCE: 24
gcgctcagca gccccttgag tccag                                    25

<210> SEQ ID NO 25
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 25
gctcgcactt agcctgttaa ggggt                                    25

<210> SEQ ID NO 26
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 26
ggacgagccc ctaggggtca ccggt                                    25

<210> SEQ ID NO 27
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 27
ggtcatgcta tccccctctg aagac                                    25

<210> SEQ ID NO 28
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 28
ggtccgagcg aactgggacc atctc                                    25

<210> SEQ ID NO 29
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 29
gtatacgttt ctaatttgta gttaa                                    25

<210> SEQ ID NO 30
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 30
gttagctatc gttcgcgaga aagtt                                    25
```

```
<210> SEQ ID NO 31
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 31
tacagtcgat atttatgcga ttcta                                   25

<210> SEQ ID NO 32
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 32
tacgttccaa atgcagcgag ctcgt                                   25

<210> SEQ ID NO 33
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 33
tagagaccat tcgcgattcc atgag                                   25

<210> SEQ ID NO 34
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 34
tgtttggaca agttggactg gccgc                                   25

<210> SEQ ID NO 35
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 35
ttaagtcgtg tccttctcct acgat                                   25

<210> SEQ ID NO 36
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 36
ttatctgtca aaaccgctaa tgtcc                                   25

<210> SEQ ID NO 37
<211> LENGTH: 25
<212> TYPE: DNA
<213> ORGANISM: Artificial Sequence
<220> FEATURE:
<223> OTHER INFORMATION: non-naturally occurring sequence
```

```
<400> SEQUENCE: 37
ttggaccgtt aattcatata tcgaa                                      25

<210> SEQ ID NO 38
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 38
ttggcagtgt aggggttatc taagc                                      25

<210> SEQ ID NO 39
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 39
tttatccgat cgtttatatg ggcgt                                      25

<210> SEQ ID NO 40
<211> LENGTH: 25
<212> TYPE: DNA
<213> ORGANISM: Artificial Sequence
<220> FEATURE:
<223> OTHER INFORMATION: non-naturally occurring sequence

<400> SEQUENCE: 40
ttttccacta ttatctttac tccgg                                      25
```

NON-NATURALLY OCCURRING DNA SEQUENCES

SUMMARY OF THE INVENTION

The present invention provides compositions of one or more DNA molecules having nucleotide sequences (SEQ ID NOS:1-40) that do not occur in nature. Also provided are fluorescently labeled DNA molecules and DNA molecules substituted with isobases, such as isocytosine or isoguanine. The DNA molecules, or their complements, can be attached to the surface of solid substrates, such as microspheres. Kits containing the compositions and other components are further provided.

DETAILED DESCRIPTION

The present invention provides compositions comprising isolated DNA molecules having nucleotide sequences (SEQ ID NOS:1-40) that do not occur in nature. As used herein, the term "DNA molecule" means a single- or double-stranded deoxyribonucleic acid embodying the sequence of deoxyribonucleotides provided herein. The deoxyribonucleotides are typically joined by phosphodiester bonds, although in some cases, nucleic acid analogs are included that may have alternate backbones, comprising, for example, phosphoramide (Beaucage, et al., Tetrahedron, 49 (10):1925 (1993) and references therein; Letsinger, J. Org. Chem., 35:3800 (1970); Sprinzl, et al., Eur. J. Biochem., 81:579 (1977); Letsinger, et al., Nucl. Acids Res., 14:3487 (1986); Sawai, et al., Chem. Lett., 805 (1984), Letsinger, et al., J. Am. Chem. Soc., 110: 4470 (1988); and Pauwels, et al., Chemica Scripta, 26:141 (1986)), phosphorothioate (Mag, et al., Nucleic Acids Res., 19:1437 (1991); and U.S. Pat. No. 5,644,048), phosphorodithioate (Briu, et al., J. Am. Chem. Soc., 111:2321 (1989)), O-methylphophoroamidite linkages (see Eckstein, Oligonucleotides and Analogues: A Practical Approach, Oxford University Press), and peptide nucleic acid backbones and linkages (see Egholm, J. Am. Chem. Soc., 114:1895 (1992); Meier, et al., Chem. Int. Ed. Engl., 31:1008 (1992); Nielsen, Nature, 365:566 (1993); Carlsson, et al., Nature, 380:207 (1996)). Other analog nucleic acids include those with positive backbones (Denpcy, et al., Proc, Natl. Acad. Sci. USA, 92:6097 (1995)); non-ionic backbones (U.S. Pat. Nos. 5,386, 023; 5,637,684; 5,602,240; 5,216,141; and 4,469,863; Kiedrowshi, et al., Angew. Chem. Intl. Ed. English, 30:423 (1991); Letsinger, et al., J. Am. Chem. Soc., 110:4470 (1988); Letsinger, et al., Nucleosides & Nucleotides, 13:1597 (1994); Chapters 2 and 3, ASC Symposium Series 580, "Carbohydrate Modifications in Antisense Research", Ed. Y. S. Sanghui and P. Dan Cook; Mesmaeker, et al., Bioorganic & Medicinal Chem. Lett., 4:395 (1994); Jeffs, et al., J. Biomolecular NMR, 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins, et al., Chem. Soc. Rev., (1995) pp. 169 176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments; for example, PNA is particularly preferred. In addition, mixtures of naturally occurring nucleic acids and analogs can be made. Alternatively, mixtures of different nucleic acid analogs, and mixtures of naturally occurring nucleic acids and analogs may be made.

Where double-stranded, the DNA molecule can be blunt-ended, have an overhang or have a "sticky-end". Such DNA molecules can be produced by any chemical or enzymatic method known in the art. Examples of such methods include phosphoramidite synthesis or replication in vivo or in vitro by a vector, such as a plasmid. Numerous polymerases are commercially available and can be used during the synthesis of DNA molecules, such as Taq, Bst, T7, T4, E. coli. pol I, large fragment.

Isobases

The invention is not limited, however, to DNA molecules containing the naturally occurring nucleotide bases of adenine, guanine, cytosine or thymine, but can include DNA molecules where one or more bases are substituted with an isobase (Eragen Biosciences, Madison, Wis.). Two particularly useful isobases are 2'-deoxy-5-methylisocytidine (iC) and 2'-deoxy-isoguanosine (iG) (see U.S. Pat. No. 6,001,983; No. 6,037,120; No. 6,617,106; and No. 6,977,161).

Alternatively, one of the bases can be substituted with a non-naturally occurring universal bases, which will basepair with all natural bases, preferably equally well. Suitable universal bases include, but are not limited to, inosine, hypoxanthine, 5-nitroindole, acylic 5-nitroindole, 4-nitropyrazole, 4-nitroimidazole and 3-nitropyrrole. See Loakes et al., Nucleic Acid Res. 22:4039 (1994); Van Aerschot et al., Nucleic Acid Res. 23:4363 (1995); Nichols et al., Nature 369:492 (1994); Berstrom et al., Nucleic Acid Res. 25:1935 (1997); Loakes et al., Nucleic Acid Res. 23:2361 (1995); Loakes et al., J. Mol. Biol. 270:426 (1997); and Fotin et al., Nucleic Acid Res. 26:1515 (1998).

In one embodiment, a DNA molecule in the composition of the invention can have one or more non-naturally occurring sequences provided by SEQ ID NOS:1-40 or their complementary sequences. In a preferred embodiment, the DNA comprises one of SEQ ID NOS: 14, 33, 34 or 27. In other embodiments, the DNA comprises one or more of SEQ ID NOS:6, 18, 24-26, 28-32, or 35-37, or the composition has at least a second DNA that comprises such sequences. In further preferred embodiments, one of the DNA molecules in the composition comprises SEQ ID NO:37-40, 28-32, 2-5, 18-21, 35-37, 1, 6, 15, 19, 22 or 33, alone or in various combinations.

Labels

The DNA molecules are preferably labeled with any of a variety of detectable labels, as is well understood in the art. By "label" or "labeled" herein is meant that a compound has at least one element, isotope or chemical compound attached to enable the detection of the DNA molecule. In one embodiment, the label is a fluorescent label, such as an ALEXA fluor (Invitrogen, Carlsbad, Calif.). Other fluorescent labels include DYLIGHT dyes (Thermo Fisher Scientific, Waltham, Mass.), ATTO dyes (Atto-Tec, Siegen, Germany), HILYTE fluors (AnaSpec, Fremont, Calif.), and QUASAR dyes (Bio-Search Technologies, Novato, Calif.). Further detectable labels include nanocrystals, radionuclide labels or colored latex beads.

The DNA molecule may also be labeled by phosphorylation (by e.g. T4 polynucleotide kinase) or otherwise modified to facilitate a subsequent enzymatic step, such as a joining step to another molecule. Particular DNA ligases such as E. coli, T4 and Taq can be used to join the DNA molecule to another, labeled DNA molecule or to another DNA molecule encoding a sequence of interest.

In a preferred embodiment, a secondary detectable label is used. A secondary label is one that is indirectly detected; for example, a secondary label can bind or react with a primary label for detection, can act on an additional product to generate a primary label (e.g. enzymes), or may allow the separation of the compound comprising the secondary label from unlabeled materials, etc. Secondary labels find particular use in systems requiring separation of labeled and unlabeled probes, and include one of a binding partner pair; chemically modifiable moieties; nuclease inhibitors, enzymes such as horseradish peroxidase, alkaline phosphatases, luciferases, etc.

Probes

The DNA molecules provided by the invention can be useful as probes, which due to their non-naturally occurring sequences, will not result in undesirable, background, or interfering hybridization to nucleic acids from natural sources. Alternatively, they can further comprise regions that complement or can hybridize to a sequence of interest in a sample nucleic acid, such as a specific allele of a polymorphism, or even a sequence characteristic of a species or genus of interest. Accordingly, probes can be suitable for binding to known or naturally occurring sequences of interest using one domain and having a non-naturally occurring sequence domain available for binding only to a complementary sequence, which will also not occur in nature. Such complementary sequences can be immobilized to a solid substrate, as described below.

The term "probe" refers to a single-stranded DNA molecule capable of hybridizing to another single-stranded nucleic acid that has a complementary or substantially complementary nucleotide sequence, under conditions that are sufficiently stringent to allow such hybridization, but without significant hybridization of noncomplementary nucleic acids. Probes may permit a limited number of mismatched or degenerate positions as long as they are capable of hybridization for the purposes of the invention. Probes useful in the invention vary in length, according to the application, desired selectivity, and stringency used, and can be 30, 35, or 40, 50, 60, 70, 80, 90, or 100 or more nucleotides. Useful DNA molecules of a desired length or sequence can therefore be obtained by specific cutting with a restriction endonuclease. Where present, the hybridization sequence can be any length suitable for hybridization, and can be from about 5, 7, 10, 12, 15, 17, 20, 22, 25 nucleotides to about 10, 12, 14, 16, 18, 20, 22, 24, 30, 40, 50, 60, 80, 100, 200 or more nucleotides.

Decoding

Where detection of a particular DNA sequence is desired, various decoding methods can be used, described for example in U.S. Pat. No. 6,620,584; No. 7,563,576; and 7,166,431. As used herein, "decoding" does not rely solely on the use of fluorescent labels (although as described herein, the use of beads with fluorescent labels can allow the "reuse" of the decoding probes), but rather on the use of combinatorial decoding nucleic acids that are added during a decoding step. The decoding nucleic acids will hybridize either to a distinct identifier coding nucleic acid (identifier probe) that is placed on the beads, or to the bioactive agent itself, for example when the bioactive agent is a nucleic acid, at least some portion of which is single stranded to allow hybridization to a decoding probe. The decoding nucleic acids are either directly or indirectly labeled, and thus decoding occurs by detecting the presence of the label.

A useful version of decoding is "combinatorial decoding", which works as follows. The coding nucleic acids (also termed identifier probes (IP) or identifier nucleic acids) comprise a primer sequence and an adjacent decoding sequence. Each decoder (or decoding) probe comprises a priming sequence (sometimes referred to herein as an "invariant sequence"), that will hybridize to the primer sequence, and at least one decoding nucleotide, generally contained within a variable sequence. The decoder probes are made as sets, with each set generally comprising at least four subsets that each have a different decoding nucleotide at the same position i.e. the detection position, (i.e. adenine, thymidine, cytosine and guanine), with each nucleotide at the detection position (detection nucleotide) comprising a unique label, preferably a fluorophore. The decoder probes are added under conditions that allow discrimination of perfect complementarity and imperfect complementarity. Thus, the decoding probe that comprises the correct base for basepairing with the coding nucleotide being interrogated will hybridize the best, and the other three decoding probes will be washed away. The detection of the unique fluor associated with the detection nucleotide allows the identification of the coding nucleotide at that position. By repeating these steps with a new set of decoding probes that extends the position of the detection nucleotide by one base, the identity of next coding nucleotide is elucidated. Although such a decoding system may require the use of large numbers of different decoding probes, synthesis of the probes is dramatically facilitated by the use of split and mix combinatorial synthesis.

In another aspect, the hybridization sequence itself can serve as an independent identification sequence, or alternatively the hybridization sequence and the non-naturally occurring sequence can overlap. Any spatial arrangement of the hybridization sequence and the non-naturally occurring sequence relative to each other is contemplated in the invention. The probes can further contain primer sequences for use with complementary primers during a subsequent amplification step.

Contacting a probe to a sample nucleic acid can be performed in a solution-phase process in the absence of solid supports. Alternatively, the contacting step can be performed with immobilized sample nucleic acids or with immobilized probes.

Immobilization

It can be useful to immobilize the DNA molecule of the invention, or a complementary sequence, to a solid-phase substrate surface, such as a microsphere, VERACODE bead (Illumina, San Diego, Calif.), or other bead format. By "microspheres" or "beads" or "particles" is meant small discrete particles, generally microscopic. The composition of the beads will vary, depending on the class of bioactive agent and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphite, titanium dioxide, latex or cross-linked dextrans such as SEPHAROSE cross-linked agarose, cellulose, nylon, cross-linked micelles and TEFLON polymer may all be used. Other examples of solid substrates can include the interior surface of a fiber optic or a flow-cell.

The immobilization can be achieved by any conventional means, including covalent, ionic, affinity and metal-chelation bonding (for example, including the incorporation of derivatized nucleotides such as AminoLink or biotinylated nucleotides that can then be used to attach the nucleic acid to a surface, as well as affinity capture by hybridization), cross-linking, and electrostatic attachment, etc.

In a preferred embodiment, affinity capture is used to attach the DNA molecules to the beads. For example, DNA molecules can be derivatized, for example with one member of a binding pair, and the beads derivatized with the other member of a binding pair. Suitable binding pairs are as described herein for identifier/decoder probe pairs. For example, the DNA molecules may be biotinylated (for example using enzymatic incorporate of biotinylated nucleotides, for by photoactivated cross-linking of biotin). Biotinylated DNA molecules can then be captured on streptavidin-coated beads, as is known in the art. Similarly, other hapten-receptor combinations can be used, such as digoxigenin and anti-digoxigenin antibodies.

Alternatively, chemical groups can be added in the form of derivatized nucleotides, which can then be used to add the DNA molecules to the surface. Preferred attachments are covalent, although even relatively weak interactions (i.e. non-covalent) can be sufficient to attach a nucleic acid to a surface, if there are multiple sites of attachment per each DNA molecule. Thus, for example, electrostatic interactions can be used for attachment, for example by having beads carrying the opposite charge to the bioactive agent. Similarly, affinity capture utilizing hybridization can be used to attach DNA molecules to beads. If the nucleic acids of interest do not contain a poly(A) tract, one can be attached by polymerization with terminal transferase, or via ligation of an oligoA linker, as is known in the art. Alternatively, chemical crosslinking may be done, for example by photoactivated crosslinking of thymidine to reactive groups, as is known in the art.

Kits

The invention further provides a kit containing one or more compositions of the invention and including a separate component or reagents. Exemplary components include, for example, probes described herein attached to a solid support, hybridization reagents, synthesis reagents for enzymatic extension and/or ligation of nucleic acids or probes described herein, detection reagents including decoding oligonucleotides. Any of such reagents can include, for example, some, many or all of the enzymes and buffers described herein for a chemical or enzymatic reaction.

Instructions can further be included in a kit of the invention. The instructions can include, for example, procedures for making any components or articles used in the methods of the invention, performing any embodiment of the invention and/or instructions for performing any subsequent analysis and/or decoding steps. Software may also be included in the kit (or provided separately) that automates one or more of the steps.

The brief section headings are for convenience only, and are not intended to define the invention nor limit the scope of the disclosure under those headings. To provide describe the state of the art, this application refers to various patents and publications; their entire disclosures are hereby incorporated by reference. Although the invention has been exemplified by particular embodiments, those skilled in the art will readily appreciate that the spirit of the disclosed invention includes modifications that do not substantially affect the activity of the invention.

We claim:

1. A composition comprising an isolated DNA molecule comprising the sequence or the complement of SEQ ID NO:33.

2. The composition of claim 1, wherein the DNA molecule further comprises the sequence or the complement of SEQ ID NO:34.

3. The composition of claim 1, wherein the DNA molecule further comprises the sequence or the complement of SEQ ID NO:15.

4. The composition of claim 1, wherein the DNA molecule further comprises the sequence or the complement of SEQ ID NO:27.

5. The composition of claim 1, further comprising a second isolated DNA molecule comprising a sequence selected from the group consisting of the sequences or the complements of SEQ ID NOS:24-26.

6. The composition of claim 1, further comprising a second isolated DNA molecule comprising a sequence selected from the group consisting of the sequences or the complements of SEQ ID NOS:37-40.

7. The composition of claim 1, further comprising a second isolated DNA molecule comprising a sequence selected from the group consisting of the sequences or the complements of SEQ ID NOS:28-32.

8. The composition of claim 1, further comprising a second isolated DNA molecule comprising a sequence selected from the group consisting of the sequences or the complements of SEQ ID NOS:2-5 and 18-21.

9. The composition of claim 1, further comprising a second isolated DNA molecule comprising a sequence selected from the group consisting of the sequences or the complements of SEQ ID NOS:35-37.

10. The composition of claim 1, further comprising a second isolated DNA molecule comprising a sequence selected from the group consisting of the sequences or the complements of SEQ ID NOS:1, 6, 15, 19, 22 and 33.

11. The composition of claim 1, wherein the DNA molecule is fluorescently labeled.

12. The composition of claim 5, wherein at least two DNA molecules are fluorescently labeled.

13. The composition of claim 7, wherein at least two DNA molecules are fluorescently labeled.

14. The composition of claim 9, wherein at least two DNA molecules are fluorescently labeled.

15. The composition of claim 10, wherein at least two DNA molecules are fluorescently labeled.

16. The composition of claim 1, wherein a base of a DNA molecule is replaced by isocytosine or isoguanine.

17. The composition of claim 1, wherein a base of a DNA molecule is replaced by a universal base.

18. A solid substrate having the composition of claim 1 attached to the surface of the substrate.

19. The solid substrate of claim 18, wherein the substrate is a microsphere.

20. The solid substrate of claim 18, wherein the substrate is glass.

* * * * *